United States Patent [19]

Steinert et al.

[11] Patent Number: 5,527,773

[45] Date of Patent: Jun. 18, 1996

[54] USE OF SYNTHETIC PEPTIDES TO DISRUPT THE CYTOSKELETON

[75] Inventors: Peter M. Steinert, Rockville, Md.; Robert D. Goldman, Wilmette, Ill.; John J. DiGiovanna, Bethesda, Md.

[73] Assignee: United States of America, Washington, D.C.

[21] Appl. No.: 112,784

[22] Filed: Aug. 25, 1993

[51] Int. Cl.$^6$ .......................... A61K 38/10; A61K 38/18
[52] U.S. Cl. .................... 514/12; 514/13; 514/14; 514/15; 530/324; 530/326; 530/327; 530/328; 530/350; 530/357; 435/240.2; 435/240.21; 435/240.23; 435/240.24; 435/240.25
[58] Field of Search ................... 514/15, 14, 13, 514/12; 530/357, 328, 327, 326, 324, 350; 435/240.2, 240.21, 240.23, 240.24, 240.25

[56] References Cited

PUBLICATIONS

Steinert et al., J. Biol. Chem., vol. 260, No. 11 Issue of Jun. 10, pp. 7142–7149 (1985).
Steinert et al., J. of Investigative Dermatology, vol. 100, p. 500 (1993).
Johnson et al., Proc. Natl. Acad. Sci. USA, vol. 82, pp. 1896–1900, Apr. 1985.

*Primary Examiner*—Howard E. Schain
*Attorney, Agent, or Firm*—Knobbe Martens Olson & Bear

[57] ABSTRACT

Synthetic peptides corresponding to different regions of the human keratin 1 chain can disassemble preformed keratin intermediate filaments or inhibit filament assembly both in vitro and in vivo. The disruption of keratin filaments may have therapeutic applications in the treatment of epithelial abnormalities.

15 Claims, 2 Drawing Sheets

USE OF SYNTHETIC PEPTIDES TO DISRUPT THE CYTOSKELETON

FIELD OF THE INVENTION

This invention relates to the disruption of cytoskeletal elements by peptides both in vitro and in vivo. More specifically, when mixed in vitro or microinjected into cells in vivo, synthetic peptides corresponding to certain regions of intermediate filaments can dramatically alter filament and cytoskeletal organization. These alterations have implications for the treatment of various epithelial abnormalities including skin cancer and psoriasis since the disruption of keratin filaments, necessary for epithelial cell survival, will allow selective removal of these abnormalities.

BACKGROUND OF THE INVENTION

Many properties of a cell including its shape, internal organization, motility and adhesion depend on a complex network of cytoplasmic protein filaments called the cytoskeleton. The types of filaments comprising the cytoskeleton are actin filaments (microfilaments), microtubules (MTs) and intermediate filaments (IFs). In addition to the three types of filaments, the cytoskeleton contains a number of accessory proteins including vinculin, talin and α-actinin which link different filaments and connect the cytoskeleton to the plasma membrane (Alberts et al., (1983) *Molecular Biology of the Cell*, 549–609). The contents of this chapter are hereby incorporated by reference.

Actin filaments and microtubules are dynamic structures, able to rapidly assemble and disassemble to promote processes including muscle contraction and mitosis. IFs, intermediate in diameter (8–10 nm) between actin filaments and microtubules, are concentrated in areas of a cell subject to mechanical stress, such as between adjacent sarcomeres in muscle cells, and are the most stable and least soluble type of filament in the cell.

There are five distinct types of IFs which are expressed in different cell types: type I and II keratins in epithelial cells; type III IFs consisting of vimentin, desmin, glial fibrillary acidic protein and peripherin; type IV neuronal IFs (the neurofilament triplet protein) and type V nuclear lamins (Steinert and Roop (1988) *Annu. Rev. Biochem.*, 57, 593–625).

Long believed to be static, uninteresting structures, IFs are now emerging as dynamic entities. The phosphorylation-mediated reversible disassembly of both type V nuclear lamins and type III vimentin IFs during mitosis has been demonstrated (Dessev et al., (1988) *Proc. Natl. Acad. Sci. U.S.A.*, 85, 2994–2998). In addition, the dynamic phosphorylation of the human IF keratin 1 (type II) chain has also been described (Steinert, (1988) *J. Biol. Chem.* 263, 13333–13339). When epithelial cells were transfected with a mutant keratin gene, the protein was redistributed throughout the cytoskeleton after 4 days (Albers and Fuchs, (1989) *J. Cell Biol.*, 108: 1477–1493). Biotinylated keratin, when microinjected into primary mouse epidermal (PME) or kangaroo rat kidney epithelial (PtK₂) cells in vivo, incorporated rapidly (between 15 and 30 min) into keratin filament bundles called tonofilaments (Miller et al., (1991) *J. Cell Biol.*, 113: 843–855). The above data suggest that keratin IFs are dynamic structures in vivo.

All keratin chains, as well as other IF types, have a central, highly-conserved α-helical "rod" domain in regard to size, organization and likely secondary structure flanked by amino- and carboxy-"end" domains (E1, V1, H1 and E2, V2, H2). The V sequences are of highly variable size and amino acid sequence. The H1 and H2 sequences which flank the beginning and end of the rod domain, respectively, (FIG. 1) are highly conserved in sequence. In addition, there are highly conserved canonical-sequences (1A and 2B) at the beginning and end of the rod domain which are common to all IF types; however, the H1 and H2 sequences are unique to keratin IFs (Steinert and Roop, (1988) *Annu. Rev. Biochem.*, 57: 593–625).

Keratin intermediate filaments contain type I (acidic) and type II (neutral-basic) IF proteins. Both type I and type II chains have been characterized by isoelectric point, sequence similarities and immunoreactivity and are required for 10 nm filament formation at the heterodimer level. IFs can comprise up to 95% of total cell protein in keratinocytes.

Tumor necrosis factor (TNF) has been shown to alter the cytoskeletal organization of kidney mesangial cells (Camassi et al. (1990), *Kidney Intl.*, 38: 795–802). Within one to two hours after TNF administration the cells retracted and lost reciprocal contacts. Similar changes were observed after a five minute treatment with platelet activating factor (PAF).

Chipev et al. (*Cell*, 70: 821–828, (1992)) steadied epidermolytic hyperkeratosis, an autosomal dominant disease affecting the suprabasal level of the epidermis. They found that synthetic peptides corresponding to a region of the conserved H1 domain drastically affected the structural integrity of, or even totally disassembled, preformed filaments in vitro.

Hatzfeld and Weber (*J. Cell Biol.*, 116: 157–166, (1992)) showed that a synthetic peptide corresponding to a portion of the carboxy-terminal end of the "rod" domain (2B region) inhibited IF assembly and disassembled preformed filaments in vitro, while Kouklis et al. (*J. Cell Sci.*, 102: 31–41, (1992)) demonstrated that a 20-residue synthetic peptide containing the same consensus sequence (LLEGE) was able to inhibit assembly of vimentin filaments. In addition, they showed that a monoclonal antibody directed against the 2B sequence, when microinjected into interphasic 3T3 cells, resulted in disruption of vimentin IFs. Stappenbeck and Green (*J. Cell Biol.*, 116: 1197–1209, (1992)) showed that peptides derived from desmoplakins I and II, components of the desmosome which act as a cell attachment site for IFs, promoted the disruption of IFs in COS-7 and 3T3 cells. Finally, Letai et al. (*J. Cell Biol.*, 116: 1181–1195) demonstrated that proline mutations at the ends of the rod domain of keratin IFs destabilized these filaments.

Although the above findings indicated that a peptide corresponding to a sequence at the end of the keratin chain "rod" domain promoted rapid filament disassembly in vitro, the peptides used in vitro and in vivo in the present invention correspond to different regions of the keratin chain. In addition, the use of the H1 and 1A keratin 1 chain peptides for in vivo disruption of keratin and vimentin IFs has not been previously demonstrated.

Steinert et al. (*J. Invest. Dermatol.*, 100: 500, (1993)) reported that synthetic peptides corresponding to certain portions of the keratin 1 chain have significant effects on the structural organization and integrity of filaments both in vivo and in vitro. More specifically, peptides corresponding to the H1, 1A, and 2B regions of the human keratin 1 chain (FIG. 1) resulted in a rapid, reversible disassembly of the IFs in vitro. Similarly, microinjection of the 1A peptide also caused drastic, reversible disassembly of the endogenous IF network of epithelial cells and fibroblasts, due to disruption of keratin and vimentin IFs, respectively. These sequences are normally located adjacent to each other in the IF and represent key points of interaction in maintenance of IF structure and integrity. IFs are excellent cell type specific markers and represent potential cell type specific targets for drug therapy.

SUMMARY OF THE INVENTION

Figure 1:
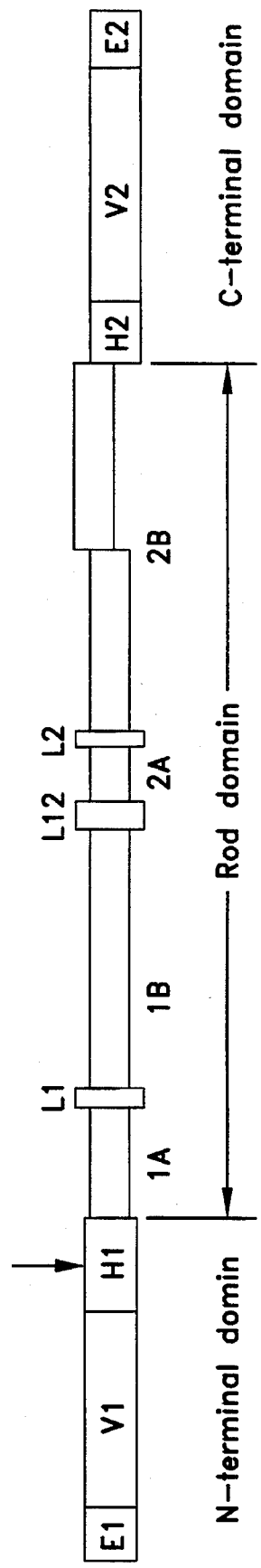
FIG. 1 is a schematic representation of the secondary structure of the keratin 1 intermediate filament chain illustrating the various subdomains.

One embodiment of the present invention is synthetic peptides having sequences corresponding to the H1 and 1A regions of the human keratin 1 chain, or fragments thereof, able to disassemble preformed IFs or to inhibit IF assembly. Preferably this disassembly or inhibition is in vitro; most preferably it is in vivo.

Another embodiment is a method for using such peptides for such disassembly or inhibition by contacting them with IFs or cells making IFs.

Still another embodiment of the present invention is a method for halting or slowing the progress of epithelial abnormalities by administering a pharmaceutically active composition of the IF assembly-inhibiting peptides. The epithelial abnormality may, for example, be skin cancer, warts, psoriasis, genetic diseases of cornification, intestinal polyps or lesions of the genitourinary tract, and the administration is either topical, intradermal, oral or by direct injection into the abnormality. The peptides are advantageously administered in a biologically compatible carrier, and may also be enclosed in a lamellar structure.

A further embodiment consists of a method for inhibiting the peptide-mediated IF disassembly by administering the L2 peptide, or active fragment thereof, to an epithelial lesion subsequent to administering the IF disassembly-inducing peptides. Preferably, this peptide is administered in a biologically compatible carrier either topically, intradermally, orally or by direct injection into the lesion. Preferably, this administration is in vitro; most preferably the administration is in vivo.

Still another preferred embodiment of the present invention is a method for enhancing the penetration of a pharmaceutically active agent by administering an active IF disassembly-inducing peptide followed by administration of the pharmaceutically active agent. In another aspect of this embodiment, the peptide and pharmaceutical agent may be administered simultaneously. Preferably this administration is either topical or oral.

DETAILED DESCRIPTION OF THE INVENTION

This invention discloses the use of synthetic peptides derived from the human keratin 1 chain H1 and 1A regions in inhibiting IF assembly and disrupting preformed filaments in vitro and the use of the 1A peptide, or fragments thereof, for disruption of IFs in vivo. This in vivo disruption will be particularly useful in the treatment of epithelial abnormalities including skin cancer, psoriasis, warts and genetic diseases of cornification. Since epithelial cells contain large amounts of keratin IFs, peptide-induced disruption of these filaments either alone or in conjunction with other pharmaceutical agents will allow the removal of these abnormalities. In addition, since the linings of the gastrointestinal and genitourinary tracts are also composed of epithelial cells, the treatment of premalignant polyps and viral lesions within these tracts by administration of these peptides is also contemplated. The L2 peptide, which itself does not interfere with IF assembly, will inhibit disassembly promoted by the H1 or 1A peptides and is useful in controlling the disassembly process after administration of the peptides. These peptides are derived from high affinity binding domains which are involved in IF polymer formation.

In addition, since these peptides are likely to be biodegradable and nonimmunogenic, they will prove less invasive and less toxic than conventional surgery or chemotherapy. Furthermore, since these peptides can disrupt IFs in the stratum corneum layer of the epidermis, thus locally disrupting and removing the outer skin layer, they may also be used to enhance the penetration of other pharmaceutically active agents.

IFs are contacted with the active peptides of the present invention in an amount effective to facilitate filament disassembly in vitro, inside cells, inside mammalian cells and, most preferably, inside human cells. It is contemplated that the filament disassembly mediated by the active peptides described in the present invention will be effective in epithelial cells from a variety of species since these filament sequences are highly conserved. In addition, synthetic H1 and 1A sequences, or fragments thereof, based on the sequences of these regions from other vertebrates will also be effective in inhibiting IF assembly or promoting IF disassembly and are also within the scope of the present invention.

The therapeutic in vivo use of peptides corresponding to the human keratin 1 1A region is contemplated since these peptides, when microinjected into cells in vivo, are able to disrupt IFs (see Example 4). Since these peptides are soluble they can be administered in either an injectable or topical form. Smaller peptides derived from this sequence able to disrupt IFs either in vitro or in vivo, such as the first 18 amino acids of the 1A peptide, are also within the scope of the present invention and, in fact, are preferable since these molecules are more likely to be directly taken up by stratified squamous epithelial cells. In addition, the use of the H1 peptide or fragment thereof to disrupt IFs in vivo, once obtained in soluble form, is also contemplated.

In addition, since the highly conserved 1A sequence is found in IFs from many cell types including neural cells and fibroblasts, the treatment of disorders involving such cell types using the 1A peptide, or fragments thereof, is also contemplated.

A screening procedure using the methods of Examples 2 and 3 can easily be used by one with ordinary skill in the art to determine, without undue experimentation, whether a specific peptide of interest derived from the keratin 1 chain H1 and 1A regions is able to inhibit IF assembly or to promote filament disassembly in vitro. If the peptide is active in vitro, then it can be tested for filament disassembly activity in vivo by the microinjection method described in Example 4.

The L2 peptide is useful in controlling the disruption of the cytoskeleton in vitro since although this peptide does not itself inhibit filament formation, it does interfere with the in vitro inhibition promoted by the H1 and 1A peptides and may also perform this function in vivo. Other peptides derived from the L2 region having filament-disassembly inhibiting activity are also within the scope of the present invention.

The peptides of the present invention can be applied topically in pharmaceutical compositions consisting of gels, ointments, creams, salves, and the like in an amount from about 1 µg to about 10 mg or more for an amount of time sufficient to promote the removal of the desired amount of the epidermal layer.

Another preferred embodiment of the present invention is the specific targeting of these peptides to different layers of the epidermis depending on the concentration of peptide used. Since the effects of the peptide are concentration-dependent, in smaller doses, only the outer layer (stratum corneum) will be disrupted upon topical administration. This will be useful for superficial epidermal disorders such as seborrhea in which deep penetration is not desired.

At higher peptide concentrations, the underlying epidermal layers will also be disrupted. This will be useful for the treatment of certain premalignant conditions such as actinic keratosis. In addition, at even higher peptide concentrations, it is contemplated that treatment of squamous cell carcinomas which have penetrated into the dermis will be feasible. Since these tumor cells are epithelial in origin, they contain a large amount of keratin which will enable the selective removal of these cells while leaving the keratin-poor dermis mostly intact. Thus, in this manner, the depth of tissue destruction can be controlled and tumor cells can be selectively targeted. This control can also be manifested in the way the peptide is delivered to the lesion; topical administration will result in shallower destruction than will direct injection into the lesion.

Depending upon the host, dosages of about 1 μg to about 1000 μg may be appropriate when only disruption of the stratum corneum is desired, while dosages of about 100 μg to about 10 mg or more may be useful in disrupting underlying layers. The optimum dosage in any particular therapy can be readily determined through empirical techniques.

A further embodiment of the present invention consists of the enhancement of penetration of other pharmaceutically active agents due to the peptide-induced disruption and removal of the epidermal layers of the skin. This will advantageously enable the treatment of deeper skin lesions without the need for organic solvents of questionable safety, such as dimethyl sulfoxide (DMSO). Active filament disassembly-inducing peptides are topically administered to an epithelial abnormality in an amount ranging from about 1 μg to about 1000 μg for an amount of time sufficient to promote removal of the outer layer of the skin as assessed by flaking of dead skin layers. The compound of interest is then topically applied to the disrupted region of the skin.

Steroids are the treatment of choice for hyperkeratotic psoriasis, a disorder in which large amounts of keratin accumulate on the scalp. The peptides of the present invention will remove these layers of keratin, thus enabling the more efficient penetration of the lesion by steroid preparations.

In addition, the concomitant use of the IF disassembly-inducing peptides with pharmaceutical agents is also within the scope of the present invention. For example, the chemotherapeutic agent 5-fluorouracil (5-FU) is used for the treatment of basal cell carcinoma but is ineffective in treating squamous cell carcinoma, presumably due to its poor penetration into the skin. The concomitant use of 5-FU and larger amounts of IF disassembly-inducing peptides will allow the deeper penetration of 5-FU to allow treatment of squamous cell carcinoma. Thus, the use of the active IF disassembly-inducing peptides of the present invention prior to or in conjunction with other pharmaceutically active agents, especially anti-inflammatory and anti-proliferative agents, is within the scope of the present invention.

The peptides may be delivered to IFs in a number of ways in pharmaceutically active carriers and may be administered topically, intradermally or by direct injection into the lesion. The peptides may also be enclosed in liposomes, by methods well known in the art, in order to increase the efficiency of peptide delivery to the cells.

The composition can be packaged and administered in unit dosage form such as an injectable composition or local preparation in a dosage amount equivalent to the daily dosage administered to a patient or as a controlled release composition. A septum sealed vial containing a daily dose of the active ingredient in either PBS or in lyophilized form is an example of a unit dosage. The amount of peptide administered will depend on the type of lesion to be treated and the depth of penetration desired. Preferably, the peptide can be administered in amounts ranging from about 1 μg per application or injection to about 10 mg or more per application or injection. Lesser amounts (from about 2 fold to about 10 fold) will be required if the peptides are incorporated into liposomes due to enhanced delivery of peptides to the cells.

Keratin chains were purified from human epidermal cells as described in the following example.

EXAMPLE 1

Purification of Keratin Chains

Human keratin chains were extracted from foreskin epidermis in 0.1M Tris-glycine, pH 8.9, 1% SDS, and separated from profilaggrin, a major epidermal protein, by selective precipitation with 0.25 volumes of 4M NaCl. The keratins were then recovered free of SDS by ion-pair extraction and redissolved in 50 mM Tris-HCl, pH 8.0, 8M urea, 1 mM EDTA, 1 mM dithiothreitol, clarified by centrifugation at 250,000×g, and concentrations of purified keratins were determined spectrophotometrically.

To demonstrate that synthetic peptides corresponding to regions of the human keratin 1 chain were able to disrupt filament assembly in vitro, peptides were synthesized and used in keratin filament disassembly assays as described in the following example.

EXAMPLE 2

Peptide Synthesis and Keratin Filament Assembly Assays

Peptides corresponding to portions of the human keratin 1 H1 chain (PVCSPGGIQEVTINQSLLQPLNVEIDPEIQKVKSRE; SEQ ID NO: 1), the human keratin 1 1A chain (REOIKSLNNQFASFIDKVRFMEOQNKVLQTKWELL; SEQ ID NO: 2), the first 18 amino acids of SEQ ID NO: 2 (1A*); SEQ ID NO: 3) and the human keratin 1 L2 chain; SKAEAETF, SEQ ID NO: 4) were synthesized by well known methods on an Applied Biosystems Model 431 peptide synthesizer and purified by HPLC. Their compositions and concentrations were confirmed by amino acid analysis.

In vitro filament assembly assays (1–1.5 mg/ml) were performed by dialysis for 2 hours each into decreasing concentrations of urea (6, 4, 2, 1 and 0M) containing 5 mM Tris-HCl, pH 7.6, 1 mM EDTA, 1 mM dithiothreitol. The concentrations of urea used were 6, 4, 2, 1 and 0M. Light scattering was measured at 310 nm in a Beckman DU65 spectrophotometer. Synthetic peptides (1–30 μl of a 0.5–2 mg/ml solution) were added to 1 ml samples of keratin filaments, incubated at 37° C., and filament assembly was measured by light scattering. The H1 peptide effectively inhibited the formation of IFs as indicated by the decreased light scattering. Samples of these reactions were also collected for visualization by electron microscopy and stopped by negative staining with freshly-prepared 0.7% uranyl acetate.

Figure 2:
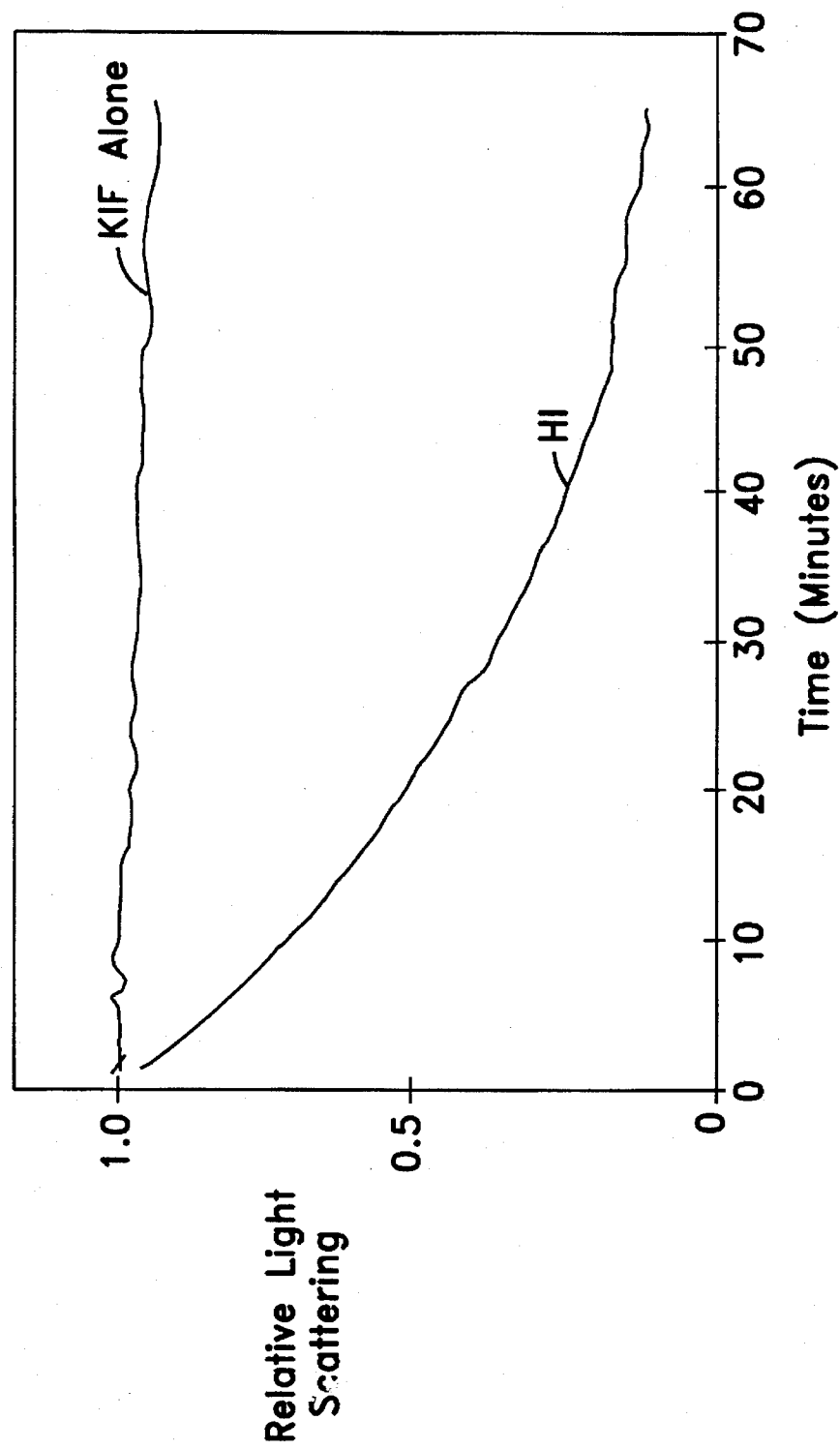
FIG. 2 shows a quantitative light scattering assay indicating the ability of the H1 peptide to disassemble preformed human keratin intermediate filaments. The time of incubation is indicated on the x-axis and the relative light scattering is indicated on the y-axis.

The results indicated that the H1 peptide was effective in inhibiting keratin filament formation in vitro as assessed by electron microscopy. Synthetic peptides were also capable of disassembling preformed keratin IFs in vitro as assessed by a rapid decrease in light scattering corresponding to filament disassembly (FIG. 2) and by electron microscopy as described below.

EXAMPLE 3

Disassembly of Preformed Keratin IFs by Synthetic Peptides

Peptides corresponding to the H1, beginning of 1A, and full-length 1A regions (SEQ ID NO: 1–3) of the human keratin 1 chain were individually mixed with preformed keratin IFs in vitro at a 1:1 molar ratio. Each peptide promoted the rapid disassembly (within 30 min) of the preformed IFs down to single coiled-coil molecules, as judged by light scattering experiments (FIG. 2) and electron microscopy, and was reversible upon removal of the peptide.

To determine whether the 1A peptide was also able to inhibit keratin IF formation in vivo, the peptide was microinjected into PtK$_2$ cells, baby hamster kidney (BHK21) cells and mouse 3T3 fibroblasts and filament integrity was assessed by electron microscopy as described in the following example.

EXAMPLE 4

Microinjection of the 1A Peptide into Cells

The synthetic peptide corresponding to the keratin 1 chain 1A region (SEQ ID NO: 2) was microinjected into PtK$_2$, BHK21 and mouse 3T3 fibroblasts according to the procedure of Vikstrom et al. (*Proc. Natl. Acad. Sci. U.S.A.,* (1989) 86: 549–553; *Methods Enzymol.,* (1991) 176: 506–525). BHK-21 cells contain type III filaments composed of vimentin and desmin, while 3T3 cells contain only vimentin. PtK$_2$ cells contain mainly keratin. Briefly, peptides in 20 mM Tris-HCl. pH 8.5, 0.17 M NaCl, 3 mM KCl were clarified by centrifugation for 30 min at 100,000×g immediately prior to microinjection. Protein concentrations in samples were determined by the method of Bradford (*Anal. Biochem.,* 72: 248–254 (1976)). Micropipettes (W-P instruments) were prepared on a micropipette puller (Industrial Science Associates). Microinjections were monitored with a Leitz Diavert phase-contrast microscope fitted with a Leitz micromanipulator according to standard techniques (Graessmann and Graessmann, (1976) *Proc. Natl. Acad. Sci. U.S.A.,* 73: 366–370; Kreis and Birchmeier, (1982) *Int. Rev. Cytol.,* 75: 209–227).

Microinjected cells were prepared for indirect immunofluorescence and confocal microscopy as described (Yang et al., (1985) *J. Cell Biol.,* 100: 620–631). IF disassembly was assessed by immunofluorescence using antibodies against IFs. At a concentration of about 0.5 mg/ml, overall cell shape was altered slightly due to the partial rounding up (loss of adhesion) after 15–20 min. Cells fixed and processed for indirect immunofluorescence at 30 min post-injection showed no significant changes in overall IF structure. At 1 mg/ml peptide, cells rounded up completely within 30 min, respreading and regaining their shape after a few hours. Immunofluorescence observations of the rounding process showed that there were disorganized arrays of IFs indicating a structural disruption had occurred. At 2–5 mg/ml, cells rounded up more quickly from their spread configurations and there were very significant alterations in both the keratin and vimentin/desmin IF networks. The rounded-up cells contained spots of fluorescence indicating a rather complete disruption of IF structure. Recovery occurred within 3–4 hours indicating a need to maintain a constant supply of peptide to maintain the disassembled state of the IF network. The 1A peptide was soluble at 5–10 mg/ml, although higher concentrations may also be obtainable.

These peptides were very specific for IFs and did not bind to or disrupt other cytoskeletal elements including microtubules and microfilaments. The effects on terminally differentiated cells, versus the immortalized cells used in this study, will most likely be more deleterious since the cells will either take much longer to recover from the disruption of the IFs or the effects will be irreversible. In the latter case, this will lead to cell death which will be of great use in proliferative and hyperplastic diseases as mentioned in the following examples.

EXAMPLE 5

Use of Keratin Synthetic Peptides for Treatment of Epithelial Abnormalities

Patients with various epithelial abnormalities including skin cancers, warts, and psoriasis are administered the synthetic 1A or 1A* peptide in a pharmaceutical composition either topically or by direct injection into the lesion in unit dosage in an amount necessary to produce the desired local concentration of peptide (from about 1 μg to about 10 mg per dose, depending on the type of lesion treated). Control patients receive only saline. Daily administration is continued until no further improvement (i.e., shrinkage and/or disappearance of the lesion) is observed.

EXAMPLE 6

Use of Synthetic Peptides to Enhance the Penetration of Pharmaceutical Agents

Psoriasis and other inflammatory skin disorders are generally treated with topical steroids. Warts are usually treated a number of ways including removal with liquid nitrogen, weak acids or by treatment with interferon. The main problem associated with these treatments is the poor penetration of agents into the lesion; it is thus desirable to enable more efficient penetration. Patients with warts or psoriasis are topically administered a filament-disassembly inducing 1A peptide or fragment thereof for from about 30 minutes to about 2 hours to allow disruption of the outer epidermal layer. Warts are then treated with interferon and psoriasis is treated with topical steroids. Alternatively, the peptide and either steroid or interferon is administered to the lesion simultaneously. Treatment is continued daily until no further improvement in the condition is observed.

While particular embodiments of the present invention have been described in detail, it will be apparent to those skilled in the art that these embodiments are exemplary, rather than limiting, and the true scope of the invention is that defined in the following claims.

What is claimed is:

1. A method for promoting disassembly or preventing assembly of cytoskeletal intermediate filaments, comprising the step of contacting said filaments with an effective amount of a peptide having from about 10 to about 100 amino acids derived from the keratin 1 H1 or 1A regions.

2. The method of claim 1, wherein said peptide is the peptide of SEQ ID NO: 1, 2, 3, or an active filament-disassembling fragment thereof.

3. The method of claim 1, wherein said filaments are in a cell.

4. The method of claim 3, wherein said cells are epithelial in origin.

5. The method of claim 1, wherein said contacting step occurs in vitro.

6. The method of claim 5, wherein said contacting step occurs in vivo.

7. A method for halting or slowing the progress of epithelial abnormalities by administering to abnormal epithelial cells a pharmaceutically active composition of a peptide having from about 10 to about 100 amino acids derived from the keratin H1 or 1A regions.

8. The method of claim 7 wherein said abnormality is selected from the group consisting of: skin cancer, warts, psoriasis, genetic diseases of cornification, intestinal polyps and lesions of the genitourinary tract.

9. The method of claim 7 wherein said administration is either topical, intradermal, oral or by direct injection into said abnormality.

10. The method of claim 7 wherein said peptide is administered in a biologically compatible carrier.

11. The method of claim 10 wherein said peptide is enclosed in a lamellar structure.

12. A method for enhancing the penetration of a pharmaceutically active agent comprising administering to a vertebrate an active intermediate filament disassembly-inducing peptide, said peptide having from about 10 to about 100 amino acids derived from the keratin 1 H1 or 1A regions, and then administering said pharmaceutically active agent to said vertebrate.

13. The method of claim 12 wherein said administration is topical.

14. The method of claim 13 wherein said administration is oral

15. The method of claim 12 wherein said intermediate filament disassembly-inducing peptide and said pharmaceutically active agent are administered simultaneously.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
    ( A ) LENGTH: 36 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i i ) IMMEDIATE SOURCE:
    ( B ) CLONE: Human keratin 1 H1 chain ( x i ) SEQUENCE DESCRIPTION: SEQ ID NO:1:

```
Pro  Val  Cys  Ser  Pro  Gly  Gly  Ile  Gln  Glu  Val  Thr  Ile  Asn  Gln  Ser
1                   5                        10                           15

Leu  Leu  Gln  Pro  Leu  Asn  Val  Glu  Ile  Asp  Pro  Glu  Ile  Gln  Lys  Val
               20                       25                      30

Lys  Ser  Arg  Glu
          35
```

( 2 ) INFORMATION FOR SEQ ID NO:2:

( i ) SEQUENCE CHARACTERISTICS:
    ( A ) LENGTH: 35 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i i ) IMMEDIATE SOURCE:
    ( B ) CLONE: Human keratin 1 1A chain ( x i ) SEQUENCE DESCRIPTION: SEQ ID NO:2:

```
Arg  Glu  Gln  Ile  Lys  Ser  Leu  Asn  Asn  Gln  Phe  Ala  Ser  Phe  Ile  Asp
1                   5                        10                           15

Lys  Val  Arg  Phe  Met  Glu  Gln  Gln  Asn  Lys  Val  Leu  Gln  Thr  Lys  Trp
               20                       25                      30

Glu  Leu  Leu
          35
```

( 2 ) INFORMATION FOR SEQ ID NO:3:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: linear ( i i ) MOLECULE TYPE: peptide (iii) HYPOTHETICAL: NO (iv) ANTI-SENSE: NO (v) FRAGMENT TYPE: internal (vii) IMMEDIATE SOURCE:
            (B) CLONE: Human keratin 1 1A chain first 18 amino acids (xi) SEQUENCE DESCRIPTION: SEQ ID NO:3:

Arg  Glu  Gln  Ile  Lys  Ser  Leu  Asn  Asn  Gln  Phe  Ala  Ser  Phe  Ile  Asp
        1                   5                        10                       15

Lys  Val (2) INFORMATION FOR SEQ ID NO:4:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
            (B) CLONE: Human keratin 1 L2 chain (xi) SEQUENCE DESCRIPTION: SEQ ID NO:4:

Ser  Lys  Ala  Glu  Ala  Glu  Thr  Phe
        1                   5